US009741084B2

(12) United States Patent
Holmes et al.

(10) Patent No.: US 9,741,084 B2
(45) Date of Patent: Aug. 22, 2017

(54) METHOD AND SYSTEM FOR PROVIDING REMOTE ACCESS TO DATA FOR DISPLAY ON A MOBILE DEVICE

(75) Inventors: Colin J. Holmes, Vancouver, WA (US); Pierre Lemire, Calgary (CA); Glenn Lehmann, Crossfield (CA)

(73) Assignee: Calgary Scientific Inc., Calgary, AB (CA)

( * ) Notice: Subject to any disclaimer, the term of this patent is extended or adjusted under 35 U.S.C. 154(b) by 594 days.

(21) Appl. No.: 13/343,105

(22) Filed: Jan. 4, 2012

(65) Prior Publication Data

US 2015/0026338 A1    Jan. 22, 2015

Related U.S. Application Data

(60) Provisional application No. 61/429,655, filed on Jan. 4, 2011.

(51) Int. Cl.
*G06F 15/167* (2006.01)
*G06Q 50/22* (2012.01)
*G06F 17/30* (2006.01)

(52) U.S. Cl.
CPC ....... *G06Q 50/22* (2013.01); *G06F 17/30905* (2013.01)

(58) Field of Classification Search
CPC ..... H04L 29/06; H04L 51/02; H04L 41/0686; H04L 63/105

(Continued)

(56) References Cited

U.S. PATENT DOCUMENTS 4,975,690 A    12/1990 Torres
5,345,550 A    9/1994 Bloomfield
(Continued)

FOREIGN PATENT DOCUMENTS

CN    102821413    12/2012
EP    0349463    1/1990
(Continued)

OTHER PUBLICATIONS

Coffman, Daniel, et al., "A Client-Server Architecture for State-Dependent Dynamic Visualization on the Web," IBM T.J. Watson Research Center, 2010, 10 pages.
(Continued)

*Primary Examiner* — Lan-Dai T Truong
(74) *Attorney, Agent, or Firm* — Meunier Carlin & Curfman LLC (57) ABSTRACT

A method and system for providing remote access to data for display on a client computer via a computer network is provided. A first and second server computer connected to a computer network execute a first and second server remote access program, respectively, for communicating with an associated first and second application program. The client computer, which is also connected to the computer network, executes a client remote access program for simultaneously communicating with the first and second server remote access programs via a first and second communication link. The first and second server remote access programs determine first and second presentation data indicative of an application state of the first and second application programs. The client remote access program receives the first and the second presentation data and determines display data in dependence thereupon for substantially simultaneously displaying the first and the second presentation data.

25 Claims, 11 Drawing Sheets

(58) Field of Classification Search
USPC ....... 709/225, 203, 201, 202, 205, 217, 218, 709/219
See application file for complete search history.

(56) References Cited

U.S. PATENT DOCUMENTS

| | | | |
|---|---|---|---|
| 5,555,003 | A | 9/1996 | Montgomery et al. |
| 5,742,778 | A | 4/1998 | Hao et al. |
| 5,844,553 | A | 12/1998 | Hao et al. |
| 5,870,759 | A | 2/1999 | Bauer et al. |
| 5,920,311 | A | 7/1999 | Anthias |
| 5,978,842 | A | 11/1999 | Noble et al. |
| 6,045,048 | A | 4/2000 | Wilz et al. |
| 6,061,689 | A | 5/2000 | Chang et al. |
| 6,075,531 | A | 6/2000 | DeStefano |
| 6,141,698 | A | 10/2000 | Krishnan et al. |
| 6,145,098 | A * | 11/2000 | Nouri et al. ................ 714/31 |
| 6,253,228 | B1 | 6/2001 | Ferris et al. |
| 6,453,334 | B1 | 9/2002 | Vinson et al. |
| 6,453,356 | B1 | 9/2002 | Sheard et al. |
| 6,570,563 | B1 | 5/2003 | Honda |
| 6,601,233 | B1 | 7/2003 | Underwood |
| 6,792,607 | B1 | 9/2004 | Burd et al. |
| 6,918,113 | B2 | 7/2005 | Patel et al. |
| 6,976,077 | B1 | 12/2005 | Lehew et al. |
| 7,065,568 | B2 | 6/2006 | Bracewell et al. |
| 7,069,227 | B1 | 6/2006 | Lintel, III et al. |
| 7,073,059 | B2 | 7/2006 | Worely et al. |
| 7,149,761 | B2 | 12/2006 | Cooke et al. |
| 7,167,893 | B1 | 1/2007 | Malone et al. |
| 7,174,504 | B2 | 2/2007 | Tsao |
| 7,181,686 | B1 | 2/2007 | Bahrs |
| 7,240,162 | B2 | 7/2007 | de Vries |
| 7,246,063 | B2 | 7/2007 | James et al. |
| 7,343,310 | B1 | 3/2008 | Stender |
| 7,350,151 | B1 | 3/2008 | Nakajima |
| 7,418,711 | B1 | 8/2008 | Lee et al. |
| 7,451,196 | B1 | 11/2008 | de Vries et al. |
| 7,577,751 | B2 | 8/2009 | Vinson et al. |
| 7,620,901 | B2 | 11/2009 | Carpenter et al. |
| 7,647,370 | B1 | 1/2010 | Liu et al. |
| 7,650,444 | B2 | 1/2010 | Dirstine et al. |
| 7,656,799 | B2 | 2/2010 | Samuels et al. |
| 7,706,399 | B2 | 4/2010 | Janczak |
| 7,725,331 | B2 | 5/2010 | Schurenberg et al. |
| 7,802,183 | B1 | 9/2010 | Essin |
| 7,831,919 | B1 | 11/2010 | Viljoen et al. |
| 7,921,078 | B2 | 4/2011 | McCuller |
| 7,941,488 | B2 | 5/2011 | Goodman et al. |
| 7,966,572 | B2 | 6/2011 | Matthews et al. |
| 8,024,523 | B2 | 9/2011 | de Vries et al. |
| 8,261,345 | B2 | 9/2012 | Hitomi et al. |
| 8,356,252 | B2 | 1/2013 | Raman et al. |
| 8,359,591 | B2 | 1/2013 | de Vries et al. |
| 8,509,230 | B2 | 8/2013 | Vinson et al. |
| 8,527,706 | B2 | 9/2013 | de Vries et al. |
| 8,572,178 | B1 | 10/2013 | Frazzini et al. |
| 8,606,952 | B2 | 12/2013 | Pasetto et al. |
| 8,627,081 | B2 | 1/2014 | Grimen et al. |
| 8,667,054 | B2 | 3/2014 | Tahan |
| 8,924,512 | B2 * | 12/2014 | Stoyanov ............... G06F 9/4445 709/203 |
| 2001/0047393 | A1 | 11/2001 | Arner et al. |
| 2002/0032751 | A1 * | 3/2002 | Bharadwaj ............... H04L 29/06 709/218 |
| 2002/0032804 | A1 | 3/2002 | Hunt |
| 2002/0092029 | A1 | 7/2002 | Smith |
| 2003/0014735 | A1 | 1/2003 | Achlioptas et al. |
| 2003/0023670 | A1 | 1/2003 | Walrath |
| 2003/0065738 | A1 | 4/2003 | Yang et al. |
| 2003/0120324 | A1 | 6/2003 | Osborn et al. |
| 2003/0120762 | A1 * | 6/2003 | Yepishin ........... G06F 17/30899 709/223 |
| 2003/0149941 | A1 | 8/2003 | Tsao |
| 2003/0163514 | A1 | 8/2003 | Waldschmidt |
| 2003/0184584 | A1 | 10/2003 | Vachuska et al. |
| 2003/0208472 | A1 | 11/2003 | Pham |
| 2004/0015842 | A1 | 1/2004 | Nanivadekar et al. |
| 2004/0029638 | A1 | 2/2004 | Hytcheson et al. |
| 2004/0039742 | A1 | 2/2004 | Barsness et al. |
| 2004/0068516 | A1 | 4/2004 | Lee et al. |
| 2004/0106916 | A1 | 6/2004 | Quaid et al. |
| 2004/0117804 | A1 | 6/2004 | Scahill et al. |
| 2004/0162876 | A1 * | 8/2004 | Kohavi ............. G06F 17/30943 709/203 |
| 2004/0183827 | A1 | 9/2004 | Putterman et al. |
| 2004/0236633 | A1 | 11/2004 | Knauerhase et al. |
| 2004/0243919 | A1 | 12/2004 | Muresan et al. |
| 2004/0249885 | A1 | 12/2004 | Petropoulakis et al. |
| 2005/0005024 | A1 | 1/2005 | Samuels et al. |
| 2005/0010871 | A1 | 1/2005 | Ruthfield et al. |
| 2005/0021687 | A1 | 1/2005 | Anastassopoulos et al. |
| 2005/0050229 | A1 | 3/2005 | Comeau et al. |
| 2005/0138631 | A1 | 6/2005 | Bellotti et al. |
| 2005/0188046 | A1 * | 8/2005 | Hickman ............. G06Q 10/107 709/206 |
| 2005/0188313 | A1 | 8/2005 | Matthews et al. |
| 2005/0240906 | A1 | 10/2005 | Kinderknecht et al. |
| 2006/0004874 | A1 | 1/2006 | Hutcheson et al. |
| 2006/0026006 | A1 | 2/2006 | Hindle |
| 2006/0031377 | A1 | 2/2006 | Ng et al. |
| 2006/0036770 | A1 | 2/2006 | Hosn et al. |
| 2006/0101397 | A1 | 5/2006 | Mercer et al. |
| 2006/0130069 | A1 | 6/2006 | Srinivasan et al. |
| 2006/0231175 | A1 | 10/2006 | Vondracek et al. |
| 2006/0236328 | A1 | 10/2006 | DeWitt |
| 2006/0271563 | A1 * | 11/2006 | Angelo .................. G06Q 10/06 |
| 2006/0288171 | A1 | 12/2006 | Tsien |
| 2006/0294418 | A1 | 12/2006 | Fuchs |
| 2007/0024645 | A1 | 2/2007 | Purcell et al. |
| 2007/0047535 | A1 | 3/2007 | Varma |
| 2007/0067754 | A1 * | 3/2007 | Chen .................. G06F 11/0778 717/127 |
| 2007/0079244 | A1 | 4/2007 | Brugiolo |
| 2007/0112880 | A1 | 5/2007 | Yang et al. |
| 2007/0120763 | A1 * | 5/2007 | De Paepe ........... G06F 3/03547 345/1.3 |
| 2007/0130292 | A1 | 6/2007 | Tzruya et al. |
| 2007/0203944 | A1 | 8/2007 | Batra et al. |
| 2007/0208718 | A1 | 9/2007 | Javid et al. |
| 2007/0226636 | A1 | 9/2007 | Carpenter et al. |
| 2007/0244990 | A1 | 10/2007 | Wells |
| 2007/0256073 | A1 | 11/2007 | Troung et al. |
| 2007/0282951 | A1 | 12/2007 | Selimis et al. |
| 2008/0134211 | A1 | 6/2008 | Cui |
| 2008/0146194 | A1 | 6/2008 | Yang et al. |
| 2008/0183190 | A1 | 7/2008 | Adcox et al. |
| 2008/0313282 | A1 | 12/2008 | Warila et al. |
| 2009/0044171 | A1 | 2/2009 | Avadhanula |
| 2009/0080523 | A1 | 3/2009 | McDowell |
| 2009/0089742 | A1 | 4/2009 | Nagulu et al. |
| 2009/0119644 | A1 | 5/2009 | de Vries et al. |
| 2009/0209239 | A1 | 8/2009 | Montesdeoca |
| 2009/0217177 | A1 | 8/2009 | DeGrazia |
| 2010/0077058 | A1 | 3/2010 | Messer |
| 2010/0131591 | A1 | 5/2010 | Thomas et al. |
| 2010/0150031 | A1 | 6/2010 | Allen et al. |
| 2010/0174773 | A1 | 7/2010 | Penner et al. |
| 2010/0205147 | A1 | 8/2010 | Lee |
| 2010/0223566 | A1 | 9/2010 | Holmes et al. |
| 2010/0268813 | A1 | 10/2010 | Pahlavan et al. |
| 2011/0138283 | A1 | 6/2011 | Marston |
| 2011/0157196 | A1 | 6/2011 | Nave et al. |
| 2011/0184993 | A1 | 7/2011 | Chawla et al. |
| 2011/0213830 | A1 * | 9/2011 | Lopez et al. .................. 709/203 |
| 2011/0222442 | A1 | 9/2011 | Cole et al. |
| 2012/0084713 | A1 | 4/2012 | Desai et al. |
| 2012/0090004 | A1 * | 4/2012 | Jeong ................ H04N 5/44513 725/39 |
| 2012/0133675 | A1 | 5/2012 | McDowell |
| 2012/0154633 | A1 | 6/2012 | Rodriguez |
| 2012/0221792 | A1 | 8/2012 | de Vries et al. |
| 2012/0226742 | A1 | 9/2012 | Momchilov et al. |
| 2012/0245918 | A1 | 9/2012 | Overton et al. |

(56) References Cited

U.S. PATENT DOCUMENTS

| | | | |
|---|---|---|---|
| 2012/0246225 | A1 | 9/2012 | Lemire et al. |
| 2012/0324032 | A1 | 12/2012 | Chan |
| 2013/0007227 | A1 | 1/2013 | Hitomi et al. |
| 2013/0031618 | A1 | 1/2013 | Momchilov |
| 2013/0046816 | A1 | 2/2013 | Thomas et al. |
| 2013/0054679 | A1 | 2/2013 | Jooste |
| 2013/0070740 | A1 | 3/2013 | Yovin |
| 2013/0117474 | A1 | 5/2013 | Ajanovic et al. |
| 2013/0147845 | A1 | 6/2013 | Xie et al. |
| 2013/0159062 | A1 | 6/2013 | Stiehl |
| 2013/0179962 | A1 | 7/2013 | Arai et al. |
| 2014/0240524 | A1 | 8/2014 | Julia et al. |

FOREIGN PATENT DOCUMENTS

| | | |
|---|---|---|
| EP | 1422901 | 5/2004 |
| JP | 2007/084744 | 3/1995 |
| JP | 2002/055870 | 2/2002 |
| JP | 2005/031807 | 2/2005 |
| JP | 2005/521946 | 7/2005 |
| RU | 2295752 | 3/2007 |
| RU | 2298287 | 4/2007 |
| RU | 2305860 | 9/2007 |
| WO | 98/58478 | 12/1998 |
| WO | 01/16724 | 3/2001 |
| WO | 02/09106 | 1/2002 |
| WO | 03/032569 | 4/2003 |
| WO | 03/083684 | 10/2003 |
| WO | 2010/060206 | 6/2010 |
| WO | 2010/088768 | 8/2010 |
| WO | 2010/127327 | 11/2010 |
| WO | 2012/127308 | 9/2012 |
| WO | 2013/024342 | 2/2013 |
| WO | 2013/024343 | 2/2013 |
| WO | 2013/109984 | 7/2013 |
| WO | 2013/128284 | 9/2013 |
| WO | 2013/153439 | 10/2013 |

OTHER PUBLICATIONS

Jourdain, Sebastien, et al., "ParaViewWeb: A Web Framework for 3D Visualization and Data Processing," International Journal of Computer Information Systems and Industrial Management Applications, vol. 3, 2011, pp. 870-877.
Microsoft Computer Dictionary, Microsoft Press, 5$^{th}$ Edition, Mar. 15, 2002, p. 624.
Mitchell, J. Ross, et al., A Smartphone Client-Server Teleradiology System for Primary Diagnosis of Acute Stroke, Journal of Medical Internet Research, vol. 13, Issue 2, 2011, 12 pages.
ParaViewWeb, KitwarePublic, retrieved on Jan. 27, 2014 from http://www.paraview.org/Wiki/ParaViewWeb, 1 page.
Remote Desktop Protocol (RDP), retrieved on May 4, 2014 from http://en.wikipedia.org/wiki/Remote_Desktop_Protocol, 7 pages.
Remote Desktop Services (RDS), Remote App, retrieved on May 4, 2014 from http://en.wikipedia.org/wiki/Remote_Desktop_Services, 9 pages.
Remote Desktop Services (RDS), Windows Desktop Sharing, retrieved on May 4, 2014 from http://en.wikipedia.org/wiki/Remote_Desktop_Services, 9 pages.
International Search Report, dated Feb. 19, 2010, in connection with International Application No. PCT/CA2009/001704.
International Preliminary Report on Patentability and Written Opinion, dated May 31, 2011, in connection with International Application No. PCT/CA2009/001704.
International Search Report, dated May 12, 2010, in connection with International Application No. PCT/CA2010/000154.
International Preliminary Report on Patentability and Written Opinion, dated Aug. 9, 2011, in connection with International Application No. PCT/CA2010/000154.
International Search Report and Written Opinion, dated Jul. 31, 2012, in connection with International Application No. PCT/IB2012/000562.
International Search Report, dated Dec. 20, 2012, in connection with International Application No. PCT/IB2012/001589.
International Preliminary Report on Patentability and Written Opinion, dated Feb. 18, 2014, in connection with International Application No. PCT/IB2012/001589.
International Search Report, dated Dec. 28, 2012, in connection with International Application No. PCT/IB2012/001590.
International Preliminary Report on Patentability and Written Opinion, dated Feb. 18, 2014, in connection with International Application No. PCT/IB2012/001590.
International Search Report and Written Opinion, dated Aug. 21, 2013, in connection with International Application No. PCT/IB2013/000676.
International Search Report and Written Opinion, dated Jul. 31, 2013, in connection with International Application No. PCT/IB2013/000720.
Fraser, Neil, "Differential Synchronization," DocEng'09, Proceedings of the 2009 ACM Symposium on Document Engineering, Sep. 16-18, 2009, Munich, Germany, pp. 13-20.
Extended European Search Report, dated Jun. 2, 2014, received in connection with European Application No. 12760310.8.
Extended European Search Report, dated Mar. 3, 2015, received in connection with corresponding European Application No. 09828497.9.
International Search Report and Written Opinion, dated Mar. 19, 2015, received in connection with International Application No. PCT/US2014/064243.
Search Report and Written Opinion, dated Nov. 16, 2015, received in connection with SG Application No. 2013087150.

* cited by examiner

METHOD AND SYSTEM FOR PROVIDING REMOTE ACCESS TO DATA FOR DISPLAY ON A MOBILE DEVICE

CROSS-REFERENCE TO RELATED APPLICATION

This application claims priority to U.S. Patent Application No. 61/429,655, entitled, "Method and System for Providing Remote Access to Data for Display on a Mobile Device," filed Jan. 4, 2011, which is incorporated herein by reference in its entirety.

BACKGROUND OF THE DISCLOSURE

In numerous present day scenarios, computer networks may provide remote access to data for display on a mobile device, and in particular to enable remote access to data that are stored in different locations. For example, in the healthcare sector a medical practitioner, such as a surgeon working at a first hospital, may want to compare medical imaging data, such as, for example, MRI data or CT Scan data of a patient captured at the first hospital with imaging data of the patient that have been previously captured at a second hospital or medical imaging facility. In another example, a medical practitioner may want to compare imaging data captured of a patient with reference imaging data stored in a medical repository.

Use of wireless handheld devices such as, for example, IPHONE, ANDROID, and IPAD has rapidly increased over the last couple of years to the extent that now nearly every professional owns at least one wireless handheld device. State of the art wireless mobile technology enables use of small wireless handheld devices to access the Internet and download various forms of image data files for display thereon.

SUMMARY OF THE DISCLOSURE

A method and system for providing remote access to data for display on a device such as a mobile device via a computer network is provided. According to some implementations, the method and system provide substantially simultaneous remote access to data stored in different locations for display on a wireless handheld device via a wireless computer network.

According to some implementations, there are disclosed methods of providing remote access to a plurality of application programs executing on plural server computers. The methods include providing at least one server remote access program on each the plural server computers, each of the plural server remote access programs being in communication with a respective one of plural application programs; providing at least one remote connection to a client remote access program executing on a client computer, the at least one remote connection enabling remote access to the plural application programs, and the client remote access program communicating with the at least one server remote access program over the at least one remote connection; communicating presentation data representing a change in a state of at least one of the plural application programs to the client remote access program; and displaying the presentation data at the client computer.

According to some implementations, there are disclosed methods of providing remote access to a plurality of application programs executing on plural server computers. The methods may include providing a server remote access program on each of the plural server computers, each server remote access program being in communication with a respective one of plural application programs; providing at least one remote connection to a client remote access program executing on a client computer, the at least one remote connection enabling remote access to the plural application programs; and communicating presentation data representing a change in a state of at least one of the plural application programs to the client remote access program.

According to some implementations, there are disclosed methods of providing remote access to a plurality of application programs executing at a client computer. The methods may include providing a client remote access program on the client computer, the client remote access program being in communication with plural server computers, each of the plural server computers executing a server remote access program that is in communication with a respective one of the plural application programs; making remote connections to each server remote access program, the remote connections enabling remote access to the plural application programs; communicating presentation data representing a change in a state of the plural application programs to the client remote access program; and displaying the presentation data at the client computer.

These and other objects and advantages may be provided by the embodiments of the disclosure, including some implementations exemplified in the description and figures.

BRIEF DESCRIPTION OF THE DRAWINGS

The accompanying drawings, which are incorporated in and constitute a part of this disclosure, illustrate various implementations. Like reference numerals are used to reference like elements throughout. In the drawings.

DETAILED DESCRIPTION OF THE DISCLOSURE

Unless defined otherwise, all technical and scientific terms used herein have the same meaning as commonly understood by one of ordinary skill in the art. While implementations of the disclosure will be described for providing substantially simultaneous remote access to imaging data stored in two different locations in a clinical environment for display on a wireless handheld device only for the sake of simplicity, it will become evident to those skilled in the art that the embodiments of the disclosure are not limited thereto, but are applicable for providing remotes access to any number of locations, various other forms of data, in numerous other present day applications, and for display on other devices such as laptop computers or personal computers.

Figure 1:
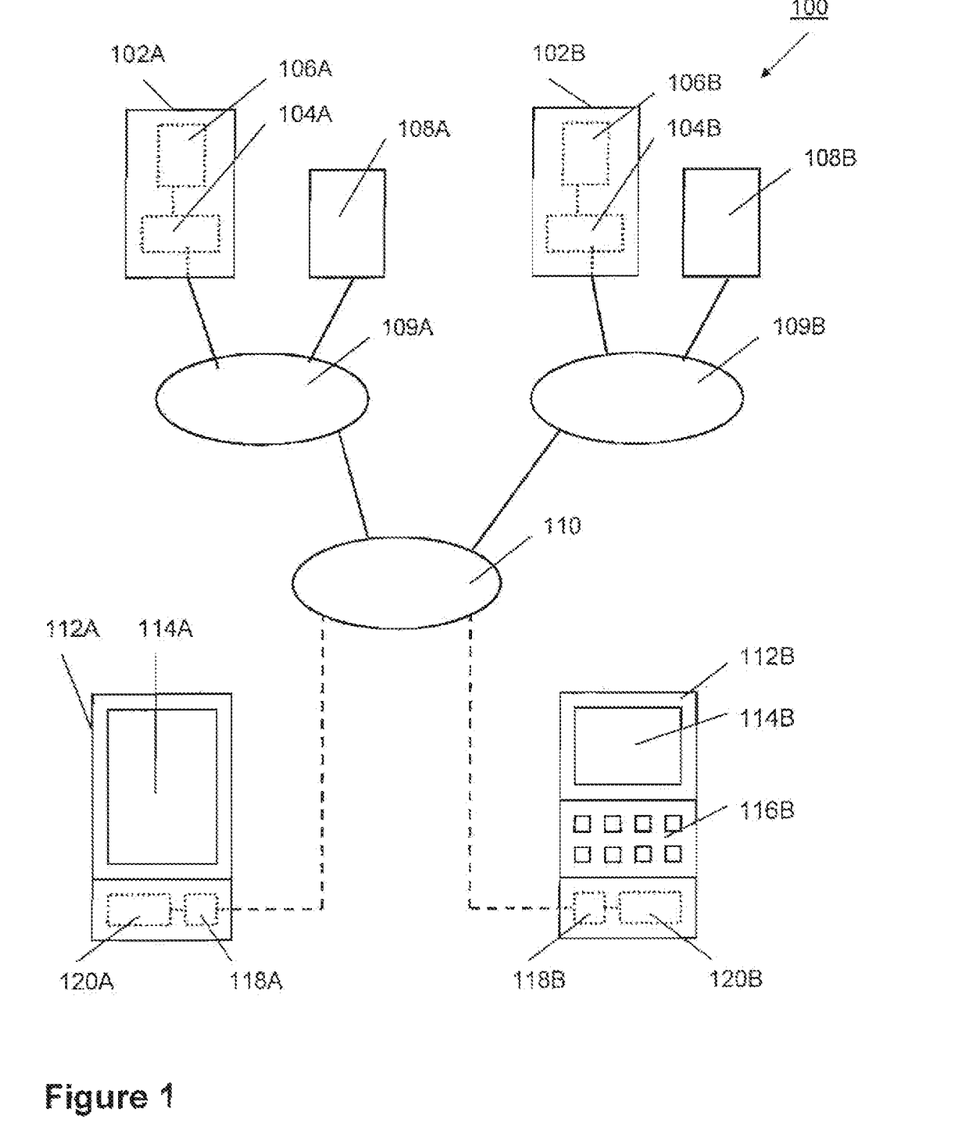
FIG. 1 is a simplified block diagram of a system for providing remote access to data for display on a mobile device via a computer network.

Referring to FIG. 1, a system 100 for providing remote access to data for display on a mobile device via a computer network according to the present disclosure is shown. The system comprises a client computer 112A or 112B, such as wireless handheld device such as, for example, an IPHONE 112A or a BLACKBERRY 112B connected via a communication network 110 such as, for example, the Internet, to a first server computer 102A and a second server computer 102B. Other client computers may be connected to the communication network 110, such as desktop computers, laptop/notebook computers, thin client devices, virtual computers, etc., that are either wired or wirelessly connected to the communication network 110.

The first server computer 102A may be connected to a first Local Area Network (LAN) 109A of a first hospital while the second server computer 102B is connected to a second Local Area Network (LAN) 109B of a second hospital. Imaging data such as, for example, MRI imaging data, CT Scan imaging data and X-ray imaging data captured at the first and the second hospital are stored in data bases 108A and 108B connected to the LANs 109A and 109B, respectively. Typically, the server computers 102A and 102B execute an electronic Picture Archiving and Communication System (PACS) using the Digital Imaging and Communications in Medicine (DICOM) format for storage and transfer. As is evident to those skilled in the art, the DICOM format is substantially unsuitable for providing remote access thereto and for displaying the same on a wireless handheld device. The PACS or other image retrieval or image processing application programs are performed, for example, by executing on the processors 104A and 104B executable commands of the respective application programs stored in memory 106A and 106B of the server computers 102A and 102B.

According to some implementations, access to data using, for example, a handheld wireless device 112A, 112B is enabled by executing: a first server remote access program on the processor 104A of the first server computer 102A; a second server remote access program on the processor 104B of the second server computer 102B; and a respective client remote access program executed on a processor 118A, 118B of the client computer 112A, 112B. The first and the second server remote access program may be performed by executing executable commands stored in the memory 106A and 106B of the first and the second server computer 102A and 102B while the client remote access program is performed by executing executable commands stored in memory 120A, 120B of the client computer 112A, 112B. An example of the server remote access program is PUREWEB, available from Calgary Scientific, Inc. of Calgary, Alberta.

Figure 2:
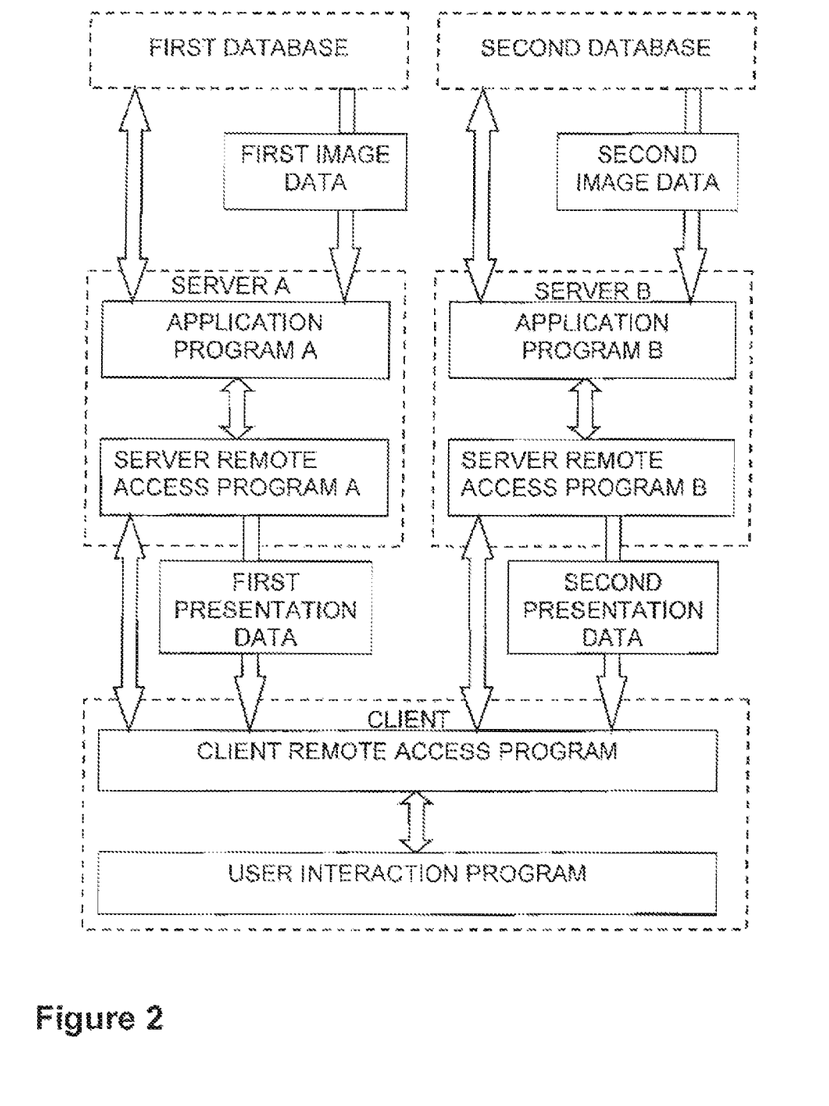
FIG. 2 is a simplified block diagram illustrating communication of a client computer with a first server computer and a second server computer of the system shown in FIG. 1.

As illustrated in FIG. 2, communication between the client computer 112A or 112B and the first and second server computer 102A and 102B is provided as communication between the first and the second server remote access program and the client remote access program via, for example, a wireless computer network. The first and the second server remote access program communicate with a respective first and second application program such as, for example, a PACS program. The first and the second application program communicate with the respective databases 108A and 108B for retrieving respective first and second image data therefrom. The client remote access program communicates with a user interaction program such as, for example, a web browser for displaying data such as, for example, image data and image processing control data; for receiving user input data for interacting with the first and the second application program using, for example, a graphical display with touch-screen 114A or a graphical display 114B and a keyboard 116B or the handheld wireless device 112A, 112B, respectively.

The first and the second server remote access program and the client remote access program may be implemented using standard programming languages and communication is enabled using standard communication technologies such as, for example, Hyper Text Transfer Protocol (HTTP), virtual private networks (VPN), and secure socket layers (SSL), which are well known to those skilled in the art. Provision of the first and the second server remote access program and the client remote access program enable implementation of aspects of the disclosure as a retrofit to existing technologies on the server side as well as on the client side.

The first and the second server remote access program receive first and second image data from the first and the second application program, respectively. Upon receipt, the first and the second server remote access program generate first and second "presentation data" of the first and second image data and transmit the same to the client remote access program. The first and second presentation data may be generated in a fashion according to hardware capabilities of the client computer 112A, 112B, for example, in accordance with processing capacity, memory size, type of graphical display, and type of user interface.

For example, presentation data generated and transmitted for a laptop computer or desktop computer are different from presentation data generated and transmitted for a handheld device such as, for example, an IPHONE. Generation of presentation data enables a substantial reduction in the amount of data transmitted for display on the small display of a handheld wireless device, i.e., results in a reduction in bandwidth utilization. Furthermore, the generation of presentation data addresses safety or privacy issues related to sensitive data such as medical imaging data by obviating the transmission of the sensitive data from the server computer to the client computer.

Figure 3A:
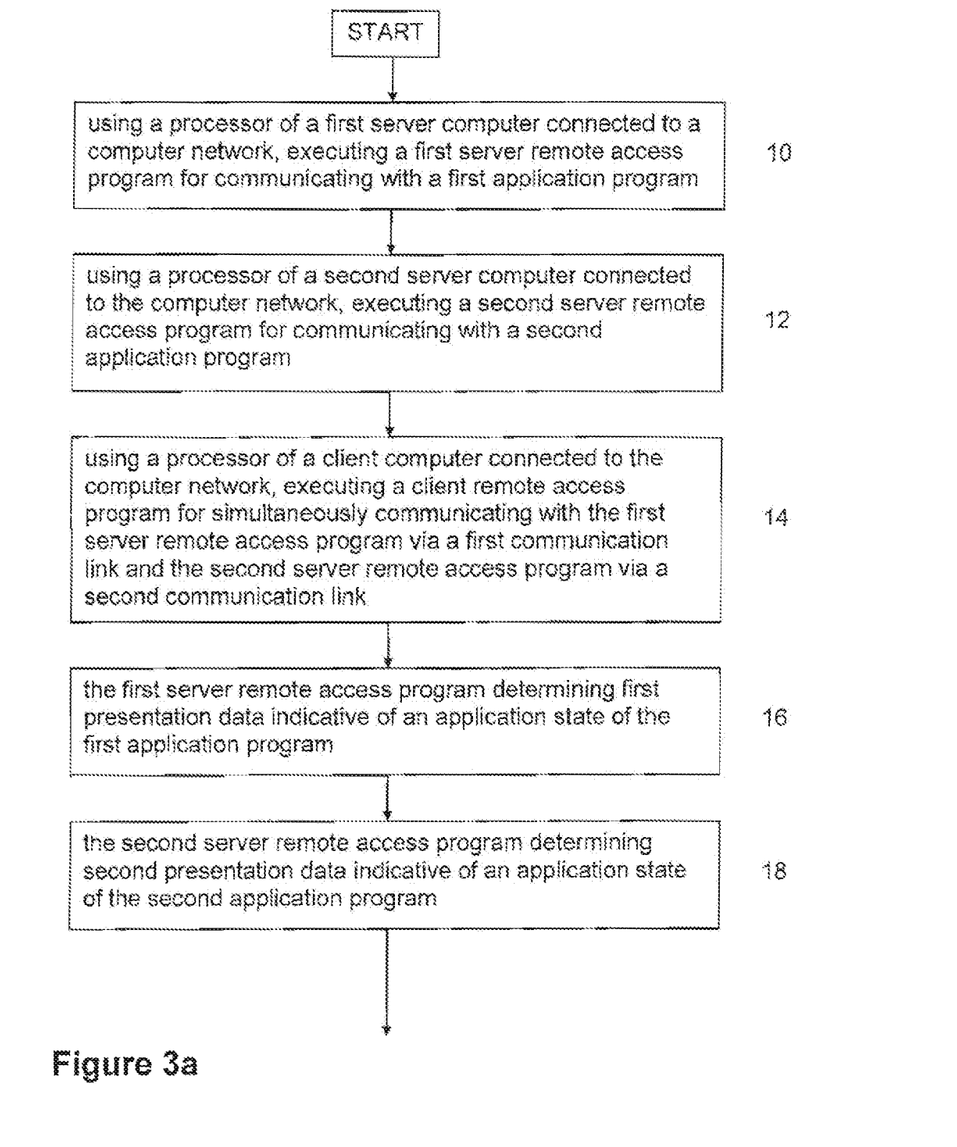
FIGS. 3a to 3c are simplified flow diagrams of a method for providing remote access to data for display on a mobile device via a computer network.

Referring to FIG. 3a, a method for providing remote access to data for display on a client computer via a computer network is shown. Using the processor 104A of the first server computer 102A connected to the computer networks 109A and 110, a first server remote access program for communicating with the first application program is executed (10). Using the processor 104B of the second server computer 102B connected to the computer networks 109B and 110, a second server remote access program for communicating with the second application program is executed (12). Using the processor 118A, 118B of the client computer 112A, 112B connected to the computer network 110, a client remote access program is executed (14) for simultaneously communicating with the first server remote access program via a first communication link—computer networks 110 and 109A—and the second server remote access program via a second communication link—computer networks 110 and 109 A. The first server remote access program determines (16) first presentation data indicative of an application state of the first application program. For example, the first server remote access program receives image data from the first application program such as a PACS program and determines first presentation data in dependence thereupon.

Optionally, at 14, the client remote access program may provide a mechanism for a single sign-on at the first server remote access program and second server remote access program to authenticate a user of the client computer with both the first server computer and second server computer. As such, the user may not be required to separately authenticate with each of the first server computer and the second server computer.

The second server remote access program determines (18) second presentation data indicative of an application state of the second application program. Preferably, the steps 16 and 18 are performed in a substantially simultaneous fashion. The client remote access program receives the first and the second presentation data and determining (20) display data in dependence thereupon for substantially simultaneously displaying the first and the second presentation data. The display data may be indicative of a single user interface as will be described herein below. Using the graphical display 114A, 114B of the client computer 112A, 112B the display data are displayed (22) in a human comprehensible fashion.

Figure 3B:
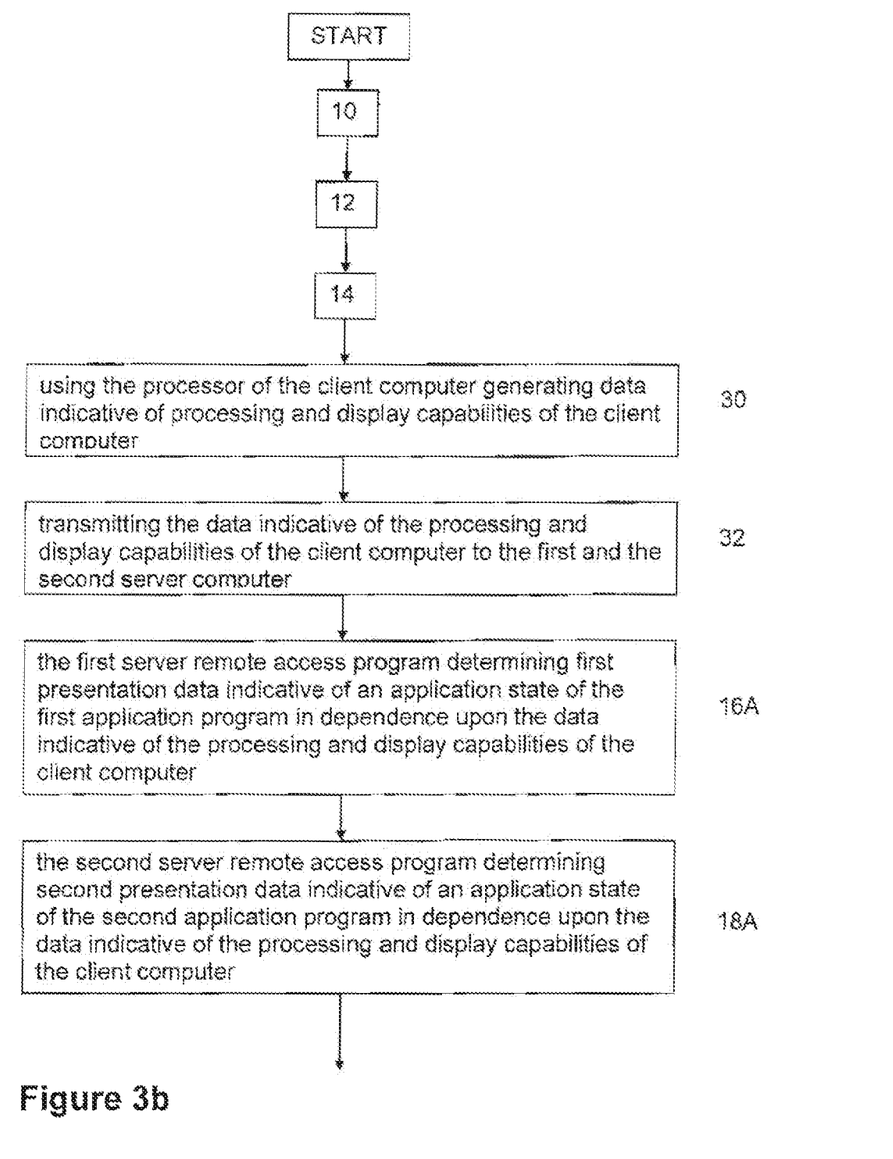

Referring to FIG. 3b, a method for providing remote access to data for display on a client computer via a computer network is shown. The method illustrated in FIG. 3b comprises the same structure as the method illustrated in FIG. 3a with same reference numerals indicating same steps. The method comprises additional steps interposed after step 14. At 30, the processor 118A, 118B of the client computer 112A, 112B generates data indicative of the processing and display capabilities of the client computer 112A, 112B and transmits the same (32) to the first and the second server remote access program executed on the first and second server computer. The first server remote access program then determines (16A) first presentation data indicative of an application state of the first application program in dependence upon the data indicative of the processing and display capabilities of the client computer. For example, the first server remote access program receives image data from the first application program such as a PACS program and determines first presentation data in dependence thereupon. The presentation data are then generated in dependence upon the previously received data indicative of the processing and display capabilities such as, for example, processing capacity, volatile memory size, type and size of graphical display, and type of user interface, of the client computer 112A, 112B, such as an IPHONE, a BLACKBERRY, a desktop computer, a laptop/notebook computer, etc. The second server remote access program may determine substantially simultaneously (18A) second presentation data indicative of an application state of the second application program in dependence upon the data indicative of the processing and display capabilities of the client computer 112A, 112B.

Optionally, after receipt of the first and second presentation data (20) the processor 118A, 118B stores (34) the first and second presentation data in volatile memory of the client computer 112A, 112B, for example, until the present communication with the first and the second server computer 102A and 102B is terminated.

For example, the steps 30 and 32 are performed during initiation of the communication with the first and the second server remote access program, Using the processor 118A, 118B of the client computer 112A, 112B first request data indicative of a first request for provision of data indicative of the state of the first application program are generated, Using the processor 118A, 118B of the client computer 112A, 112B second request data indicative of a second request for provision of data indicative of the state of the second application program are generated. Preferably, the request data comprise data indicative of the processing and display capabilities of the client computer 112A, 112B. The first request data are then transmitted to the first sever computer 102A and the second request data are transmitted to the second server computer 102B, preferably, in a substantially simultaneous fashion.

Referring to FIGS. 3c and 4a to 4c, a method for providing remote access to data for display on a client computer via a computer network is shown. The method illustrated in FIG. 3c comprises the same structure as the method illustrated in FIGS. 3a and 3b with same reference numerals indicating same steps. The method comprises additional steps interposed after step 14. At 40, the processor 118A, 118B of the client computer 112A, 112B associates interactive functionalities of the first and the second application program with respective interaction zones 204, 304. Preferably, an interactive functionality being a same in both application programs is associated with a single interaction zone. Using the processor 118A, 118B of the client computer 112A, 112B, display data indicative of the interaction zones are generated (42). The interaction zones enable user interaction with the first and the second application program. The 118A, 118B of the client computer 112A, 112B receives (44) user input data, for example, from the touch screen 114A, determines (46) an association of the received user input data to a respective interaction zone, and provides (48) the user input data to the application program associated with the respective interaction zone.

Figure 3C:
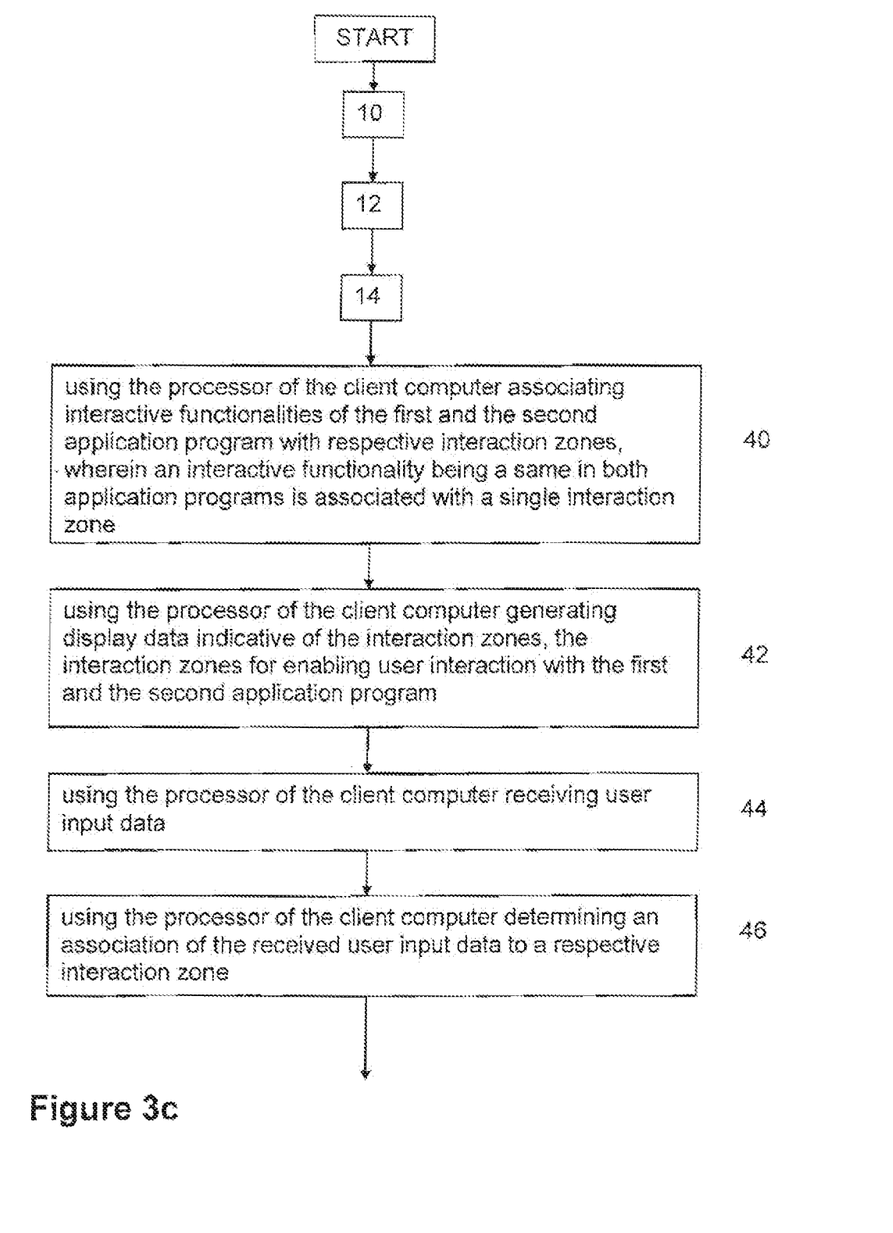

Optionally, the user input data are simultaneously provided to the first and the second application program if associated with a single interaction zone.

Further optionally, the interaction zones may not correspond to a physical display, but are associated with off-screen display buffers with sizes, color, depth, and resolution that are independent of hardware capabilities of the server computer and the client computer. The server computer then sizes the interaction zones to match each client, for example, in a round robin fashion as each connected client is updated. Alternatively, one size is used for all clients and the server computer sends interaction zone scaling instructions to each client computer for display.

The method illustrated in FIG. 3c facilitates user interaction with the application programs for, for example, zooming into a Region of Interest (ROI) in the image data, changing a view in 3D images, or performing image rendering processes.

Figure 4A:
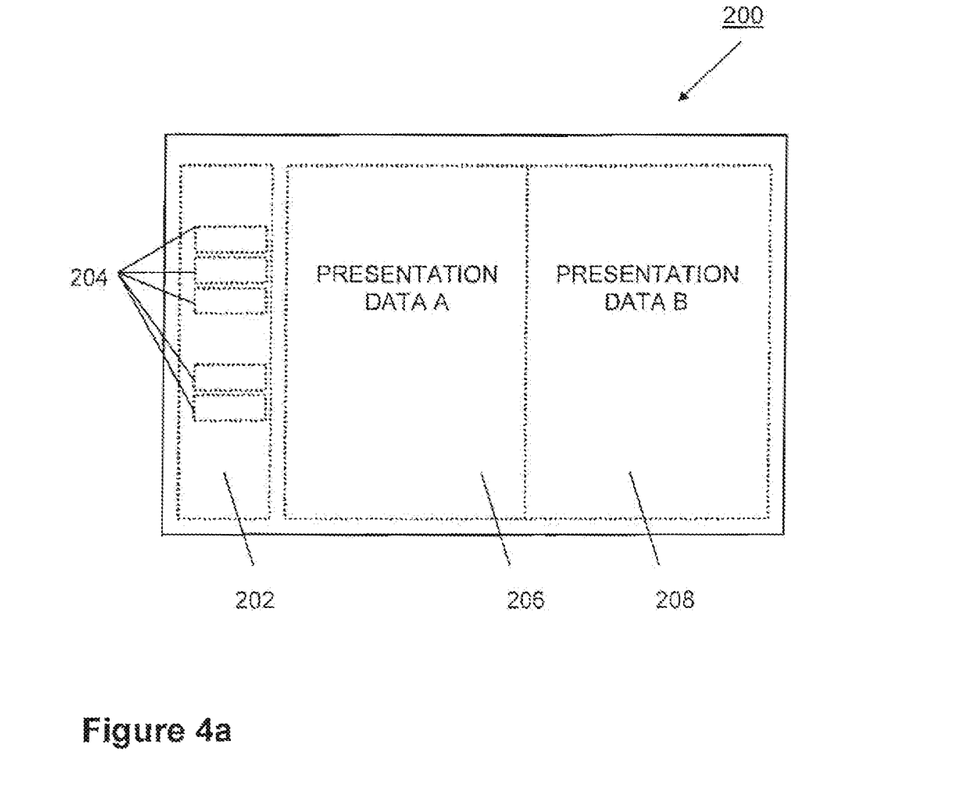
FIGS. 4a to 4c are simplified block diagrams illustrating displays for displaying the first and the second presentation data in a single user interface for use in the method illustrated in FIGS. 3a to 3c.
Figure 4B:
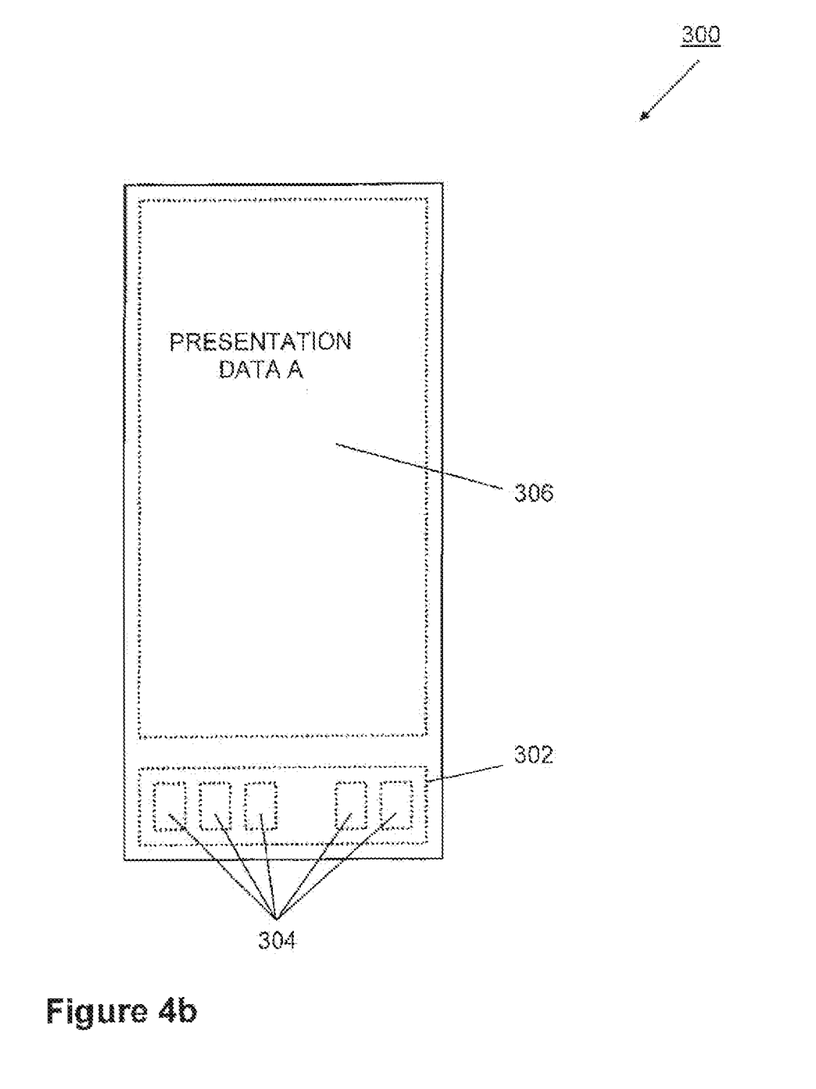
Figure 4C:
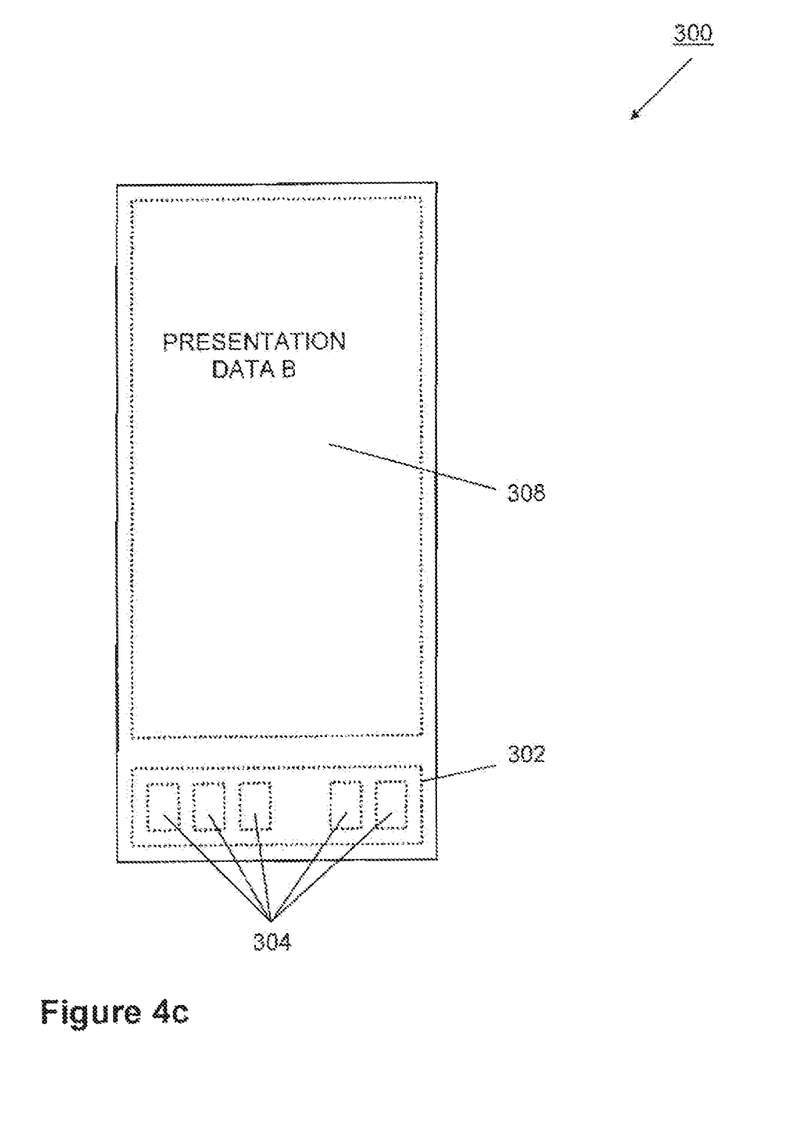

FIGS. 4a to 4c illustrate examples of displays for displaying the first and the second presentation data in a single user interface. The single user interface 200, illustrated in FIG. 4a, comprises two image display fields 206 and 208 for simultaneously displaying the first and the second presentation data, for example, in a side by side fashion. The interaction zones 204 are displayed in an interaction field 202 placed, for example, to the left hand side of the image display field 206. Other display options include placing: the display fields 206 and 208 on top of each other; the interaction field in different locations on the screen; the interaction zones in a plurality of different locations on the screen. Optionally, the user of the client computer 112A, 112B is enabled to place the various fields and/or interaction zones using, for example, drag and drop technology.

The single user interface 300, illustrated in FIGS. 4b and 4c, comprises one image display field 306 or 308 displayed in FIGS. 4b and 4c, respectively, for substantially simultaneously displaying the first and the second presentation data by flipping between the display fields 306 and 308. Each display field 306 and 308 is displayed together with the interaction zones 304 in interaction field 302. The single user interface 300 enables display of the presentation data on small displays of handheld wireless devices such as, for example, an IPHONE.

Of course, the methods for providing remote access to data for display on a client computing via a computer network according to the present disclosure is not limited to the computer network architecture illustrated in FIGS. 1 and 2. For example, the LANs 109A, 109B may be omitted and the first and the second server computer 102A may be directly connected to the computer network 110 with the databases 108A and 108B being directly connected to the respective first and second server computers 102A, 102B.

The present disclosure has been described herein with regard various implementations. However, it will be obvious to persons skilled in the art that a number of variations and modifications can be made without departing from the scope of the disclosure as described herein.

What is claimed is:

1. A method of providing remote access to a plurality of application programs executing on plural server computers, comprising:
   providing at least one server remote access program on each the plural server computers, each of the plural server remote access programs being in communication with a respective one of plural application programs;
   providing at least one remote connection to a client remote access program executing on a client computer, the at least one remote connection enabling remote access to the plural application programs, and the client remote access program communicating with the at least one server remote access program over the at least one remote connection;
   communicating presentation data representing a change in a state of each of the plural application programs to the client remote access program, the communicating to the client remote access program being performed using standard communications technologies; and
   displaying the presentation data at the client computer.

2. The method of claim 1, wherein the client remote access communicates with a user interaction program.

3. The method of claim 2, wherein the user interaction program comprises a web browser.

4. The method of claim 1, wherein the standard communications technologies include one of Hyper Text Transfer Protocol (HTTP), virtual private networks (VPN) and secure socket layers (SSL).

5. The method of claim 1, further comprising determining the presentation data in accordance with hardware capabilities of the client computer.

6. The method of claim 5, wherein the hardware capabilities comprise one of processing capacity, memory size, type of graphical display and type of user interface.

7. The method of claim 5, further comprising communicating the hardware capabilities of the client computer to the plural server remote access programs.

8. The method of claim 1, further comprising substantially simultaneously displaying, in accordance with the presentation data, a user interface associated with each of the plural application programs.

9. The method of claim 1, further comprising:
   defining interaction zones on a display of the client computer; and
   associating interactive functionalities of each of the plural application programs a respective interaction zone.

10. The method of claim 9, wherein a same interactive functionality of the plural application programs are associated with a same interaction zone.

11. The method of claim 9, further comprising:
    providing the at least one remote connection to plural client remote access programs executing on plural client computers;
    communicating presentation data representing a change in a state of at least one of the plural application programs to the plural client remote access programs; and
    displaying the presentation data at the plural client computer.

12. The method of claim 11, further comprising:
    associating the interaction zones with off-screen display buffers having characteristics that are independent of hardware capabilities of either of the plural server computers and the plural client computers; and
    sizing, by at least one of the plural server computers, the interaction zones to match each client computer in a round robin fashion as each client computer connected to the plural server computers is updated.

13. The method of claim 12, further comprising:
    defining the interaction zones having one size for all of the plural client computers; and
    sending interaction zone scaling instructions to each client computer for display.

14. The method of claim 1, further comprising:
    providing the at least one remote connection to plural client remote access programs executing on plural client computers;
    communicating presentation data representing a change in a state of at least one of the plural application programs to the plural client remote access programs; and
    displaying the presentation data at the plural client computer.

15. The method of claim 1, further comprising capturing changes in the state of the application program in the presentation data since a last presentation data was communicated by the client computer or at least one of the plural server computers.

16. The method of claim 15, wherein the presentation data captures changes in the state of the application program since the state of the application was last received by the server computer or the client computer.

17. A non-transitory computer readable medium comprising computer executable instructions that when executed by a processor of a computing device perform a method of providing remote access to a plurality of application programs executing at a client computer, comprising:
    providing a client remote access program on the client computer, the client remote access program being in communication with plural server computers, each of the plural server computers executing a server remote access program that is in communication with a respective one of the plural application programs;
    making remote connections to each server remote access program, the remote connections enabling remote access to the plural application programs;
    communicating presentation data representing a change in a state of the plural application programs to the client remote access program, the communicating to the client remote access program being performed using standard communications technologies; and
    displaying the presentation data at the client computer.

18. The non-transitory computer readable medium of claim 17, further comprising instructions for:
    determining the presentation data in accordance with hardware capabilities of the client computer; and
    simultaneously displaying, on a display associated with the client computer and in accordance with the presentation data, a user interface associated with each of the plural application programs.

19. A method of providing remote access to a plurality of application programs executing on plural server computers, comprising:
   providing at least one server remote access program on each the plural server computers, each of the plural server remote access programs being in communication with a respective one of plural application programs;
   providing at least one remote connection to a client remote access program executing on a client computer, the at least one remote connection enabling remote access to the plural application programs, and the client remote access program communicating with the at least one server remote access program over the at least one remote connection;
   communicating the hardware capabilities of the client computer to the plural server remote access programs;
   determining the presentation data representing a change in a state of at least one of the plural application programs to the client remote access program in accordance with hardware capabilities of the client computer;
   communicating the presentation data to the client remote access program, the communicating to the client remote access program being performed using standard communications technologies; and
   displaying the presentation data at the client computer.

20. The method of claim 19, wherein the client remote access communicates with a user interaction program.

21. The method of claim 19, wherein the hardware capabilities comprise one of processing capacity, memory size, type of graphical display and type of user interface.

22. The method of claim 19, further comprising substantially simultaneously displaying, in accordance with the presentation data, a user interface associated with each of the plural application programs.

23. The method of claim 19, further comprising:
   providing the at least one remote connection to plural client remote access programs executing on plural client computers;
   communicating presentation data representing a change in a state of at least one of the plural application programs to the plural client remote access programs; and
   displaying the presentation data at the plural client computer.

24. The method of claim 19, further comprising capturing changes in the state of the application program in the presentation data since a last presentation data was communicated by the client computer or at least one of the plural server computers.

25. The method of claim 24, wherein the presentation data captures changes in the state of the application program since the state of the application was last received by the server computer or the client computer.

* * * * *

UNITED STATES PATENT AND TRADEMARK OFFICE
CERTIFICATE OF CORRECTION

PATENT NO. : 9,741,084 B2
APPLICATION NO. : 13/343105
DATED : August 22, 2017
INVENTOR(S) : Colin J. Holmes et al.

It is certified that error appears in the above-identified patent and that said Letters Patent is hereby corrected as shown below:

On the Title Page

Item (75), Line 2, Column 1 Line 6 "Glenn" should read --Glen--

Signed and Sealed this
Twenty-second Day of May, 2018

Andrei Iancu
*Director of the United States Patent and Trademark Office*